(12) United States Patent
Engstrom

(10) Patent No.: US 6,436,038 B1
(45) Date of Patent: Aug. 20, 2002

(54) ANIMAL VITAL SIGNS MONITORING SYSTEM

(76) Inventor: Clarissa Engstrom, Flat 2F3 139 Buccleuch St., Edinburgh (GB), EH89NE (*) Notice: Subject to any disclaimer, the term of this patent is extended or adjusted under 35 U.S.C. 154(b) by 0 days.

(21) Appl. No.: 09/637,458

(22) Filed: Aug. 11, 2000

(51) Int. Cl.[7] .............................. A61B 5/02; A61B 5/08
(52) U.S. Cl. .................... 600/301; 600/490; 600/493; 600/500; 600/529
(58) Field of Search .............................. 600/301, 300, 600/485, 490, 499, 493, 494, 495, 500, 501, 502, 529, 549

(56) References Cited

U.S. PATENT DOCUMENTS

| | | | |
|---|---|---|---|
| 3,999,537 A | 12/1976 | Noiles | 128/2 R |
| 4,090,504 A | 5/1978 | Nathan | 128/2.05 R |
| 4,202,353 A * | 5/1980 | Hirsch et al. | 600/537 |
| D268,333 S | 3/1983 | Kojima et al. | D10/57 |
| 4,512,668 A | 4/1985 | Ivins | 374/194 |
| 4,546,775 A | 10/1985 | Medero | 128/681 |
| D287,473 S | 12/1986 | Ueno | D10/57 |
| 4,671,296 A | 6/1987 | Aitken | 128/671 |
| D298,219 S | 10/1988 | Muller | D10/57 |
| 4,854,328 A | 8/1989 | Pollack | 128/736 |
| 4,865,044 A | 9/1989 | Wallace et al. | 128/736 |
| 4,981,139 A * | 1/1991 | Pfohl | 600/484 |
| D315,520 S | 3/1991 | Murray et al. | D10/57 |
| 5,017,019 A | 5/1991 | Pompei | 374/133 |
| 5,022,402 A | 6/1991 | Schieberl et al. | 128/671 |
| 5,100,127 A | 3/1992 | Melnick et al. | 119/29 |
| 5,265,620 A | 11/1993 | Fisher | 128/736 |
| 5,309,916 A | 5/1994 | Hatschek | 128/672 |
| 5,343,869 A * | 9/1994 | Pross et al. | 600/301 |
| 5,682,898 A * | 11/1997 | Aung et al. | 600/484 |
| 5,730,147 A | 3/1998 | Craig | 128/736 |
| 5,800,349 A | 9/1998 | Isaacson et al. | 600/323 |
| 5,853,005 A | 12/1998 | Scanlon | 128/662.03 |
| 6,030,342 A * | 2/2000 | Amano et al. | 600/500 |

* cited by examiner

Primary Examiner—Kevin Shaver
Assistant Examiner—Navin Natnithithadha
(74) Attorney, Agent, or Firm—Michael E. Mauney

(57) ABSTRACT

A device for monitoring vital signs in animals. A rectal thermometer is mounted on a probe and connected to a handle. A central processing unit in the handle displays the temperature recorded by the thermometer. Also connected to the handle is a cuff used for pulse monitoring. The handle has a timer to measure an elapsed time and to sound a tone in response to a determined amount of time passing. In some application the cuff may have a blood pressure monitor so the device can measure temperature, pulse, blood pressure, and to record and sound a tone noting the elapse of a predetermined time to aid in counting respirations.

12 Claims, 3 Drawing Sheets

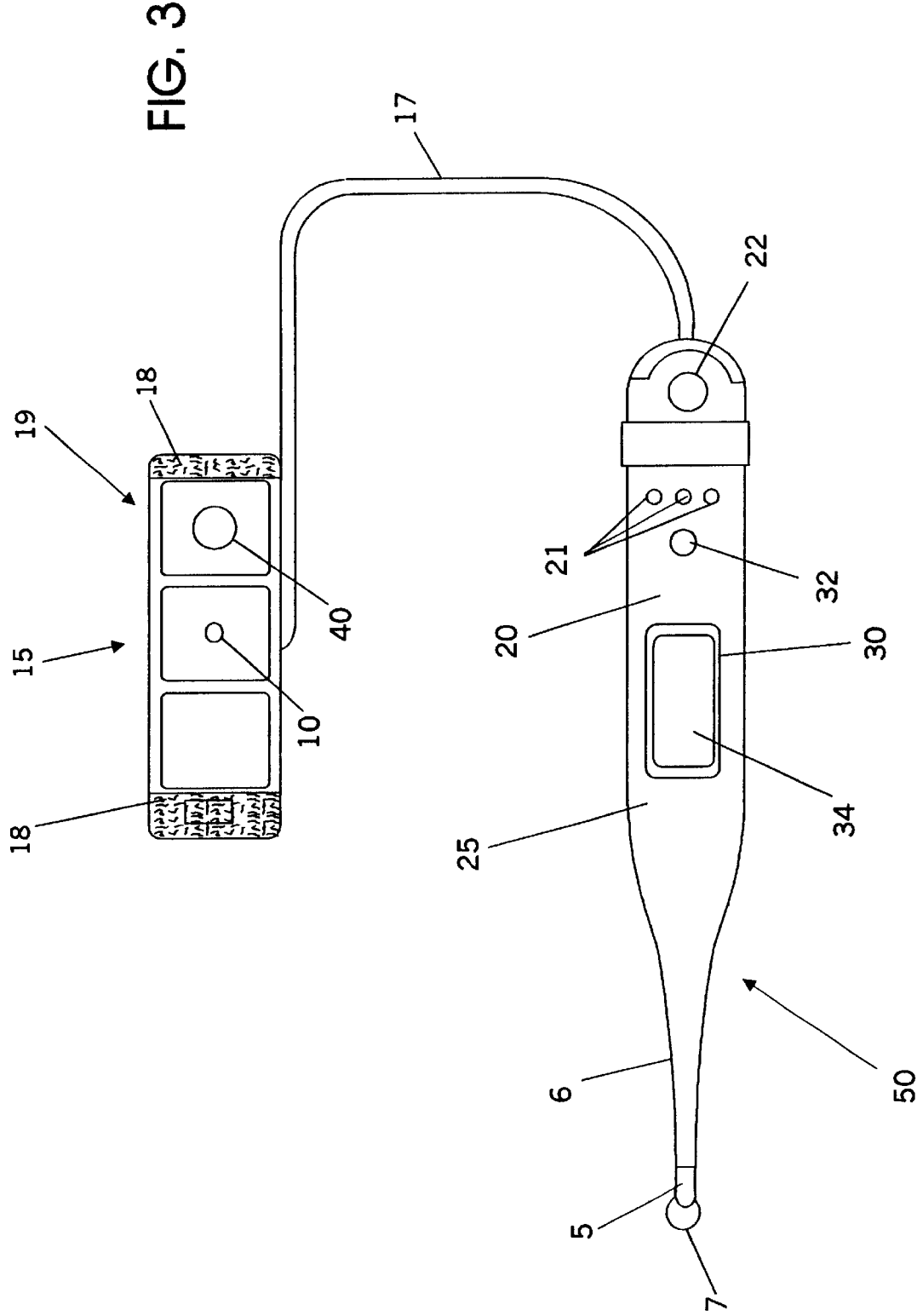

ANIMAL VITAL SIGNS MONITORING SYSTEM

FIELD OF THE INVENTION

This relates generally to a device for monitoring vital signs in animals and, more specifically, to a thermometer combined with pulse monitoring and a timer to aid in determining respirations in both large and small animals. This device may have a blood pressure monitor for some limited applications primarily in veterinary medicine office applications.

BACKGROUND OF THE INVENTION

A wide variety of devices have been proposed and developed to monitor vital signs in a patient. These range from simple digital thermometers to rather complicated devices that use light transmission to determine blood oxygen levels and pulse rates. Interestingly enough, there is some similarity in devices that are used in pediatric medicine with devices used in veterinary medicine. In both cases the patients cannot be reasoned with and consequently you cannot explain the need for an invasive, possibly painful, procedure and the patient may become restive, if not downright hostile, as the doctor, nurse, or technician goes about taking vital signs. Consequently, a wide variety of devices have been developed, both in human and veterinary medicine, to assist with these procedures.

For example, in Isaacson et al., U.S. Pat. No. 5,800,349, a transmittance pulse oximeter sensor is proposed requiring an off-set between the emitter and detector to increase the effective measuring distance for the arterial blood component leading to an improved signal and improved accuracy in the readings. This device is proposed for use not only for infants who often have the pulse oximeter placed on their ear, finger, or toe, where there is minimal tissue, but also for use in veterinary application to monitor small animals, again, whose optimal pulse oximeter location is the necessarily thin tongue tissue. In an animal application the animal would need to be anesthetized for this device to be used. This device measures arterial blood oxygen saturation as well as the pulse of the patient. However, it does nothing to check temperature, respiration rate, or blood pressure.

Noiles, U.S. Pat. No. 3,999,537, proposes a temperature pulse and respiration detector for oral use, including a therm opile and electrodes. The patient holds the housing in one hand and places the probe in his mouth. The therm opile detects the patient's temperature and respiration and the pulse rate is derived from the electrical activity sensed by the electrodes. This is for human use only.

Scanlon, U.S. Pat. No. 5,853,005, proposes using a transducer in communication with fluid in a pad to monitor acoustic signals transferred into the fluid. Typically, the acoustic signal may represent a heartbeat or breathing of a patient against whom the fluid pad is applied. Scanlon anticipates this could be used in a variety of applications, including monitoring for Sudden Infant Death Syndrome (SIDS), apnea, blood pressure cuffs, and the like.

Pollack, U.S. Pat. No. 4,854,328, proposes an animal monitoring device embedded in the animal to detect the deep body temperature of the animal and then transmit the data to a receiver which will record and monitor the condition of the animal. This could also be used to provide an identification signal providing ownership information and theft protection for stray animals.

Melnick et al., U.S. Pat. No. 5,100,127, proposes an exercise treadmill primarily for horses, particularly thoroughbred race horses. A flexible sling passes underneath the abdominal area of the quadraped. A variety of sensors are placed throughout the device to monitor the condition of the race horse.

Aitken, U.S. Pat. No. 4,671,296, proposes a pressure sensitive transducer mounted on a rectal probe. The transducer detects pressure variations caused by respiration and by the pulse, which can be calculated and displayed on a console connected to the probe. The instrument also has a thermocouple to display temperature. This is a specialized device designed primarily to check the qualitative measurement of the athletic condition of race horses.

Craig, U.S. Pat. No. 5,730,147 discloses a combined thermometer and fecal sampling apparatus primarily for animal use. It allows fecal sampling and measurement of body temperature with one application. It simplifies the taking of temperature and fecal sampling requiring only one penetration of the rectal cavity, thus is less traumatic to the animal undergoing these procedures.

Despite these devices, a Doctor of Veterinary Medicine, a veterinary technician, or a pet owner may still have difficulty in obtaining the temperature, respiration, pulse, and blood pressure in a quick and usually non-invasive manner for an awake animal The usual procedure is to insert a rectal thermometer for a set period of time—one to two minutes. Then the thermometer must be held in place by the technician, doctor, or pet owner. It is difficult to take a pulse while holding the thermometer in place. For this reason, these separate vital signs are rarely taken at the same time. After the temperature is taken, the pulse then is taken by finding an artery and counting the heartbeats for some predetermined portion of a minute, say 15 seconds, then using an appropriate multiplication factor (four (4) for a 15-second count). It is necessary to use a stethoscope to perceive the heartbeat in some animals. The pulse rate per minute is determined. Likewise, respirations are counted by observation or by touch at an interval and again usually multiplies are used to arrive at a respiration rate for one minute. This procedure requires that two different observations occur at the same time—that is, that the pulse or respiration be counted while a second hand on a watch or on a wall clock is observed to be assure the appropriate time interval is determined. To take these different observations simultaneously is a skill that must be acquired. However, even for skillful clinicians, this can be difficult to do where the animal is restive or where there may be other distractions. Frequently, the count for the parameter observed (pulse rate or respirations) may be lost or the count of the elapsed time may be lost, or even more inaccurate readings are obtained because of a lost count on untimed intervals. For some animals, taking the measurements can result in the animal taking defensive action. For example, a horse may kick someone standing behind the horse. For zoo or wild animals the animal must be sedated, but the shorter sedation time the better. Thus, speeding the process of taking vital signs is a desirable outcome. Consequently, it would be an advance in the art to provide a quick and convenient device made of existing materials and technology that would simplify obtaining the vital signs of an animal being examined, including in most applications respiration, temperature, and pulse rate.

Blood pressure measurement in animals, especially small animals, is difficult Accurate blood pressure measurement can be done by an arterial puncture with a catheter with a pressure transducer, and monitor. This direct blood pressure measurement made inside the artery by the pressure transducer is accurate. However, this arterial puncture procedure is difficult in a conscious animal and for many animals being held while an artery is punctured and a catheter inserted may well change the blood pressure. This is the type of blood pressure measurements used in animals undergoing surgery that are anesthetized.

There are methods for indirect blood pressures. These are ordinarily used with a cuff constricting a peripheral artery on either a leg or the tail. A transducer is placed distal to the cuff to detect blood flow or arterial wall motion. A variety of technologies are used in the transducer to detect blood flow or arterial wall motion from which a blood pressure is calculated. An ultrasonic, oscillometric, or photoplethysmographic technology can be used for the transducer. The ultrasonic doppler technology detects blood flow as a change in the frequency of reflected sound due to motion of the underlying red blood cells. Oscillometric technology uses pressure fluctuations produced in the cuff that is occluding the artery which results from the pressure created by the pulse inside an artery. Because the pressure fluctuations are directly dependent on the pulse rate, not only the systolic and diastolic blood pressures may be displayed, but also the pulse rate. Photoplethysmographic technology measures arterial volume by its effect on an infrared radiation. This technology is best employed in small dogs and cats weighing less than 25 pounds. Today each of these technologies have drawbacks. First, the very act of measuring the blood pressure may cause anxiety in the animal who does not understand the procedure and does not appreciate something being placed on its tail or a limb. Secondly, the technologies themselves vary in their accuracy. In practice it has been found that technologies employing the doppler principle are most accurate for cats where the oscillometric or doppler are equally accurate for dogs. Additionally, the doppler method requires, for most accurate results, that an area be shaved and acoustic gel be applied at the site of the transducer placement. However, technological advances are expected in these areas and more reliable means of determining blood pressure at or near the site of an occluding cuff are likely to be developed within a few years.

Consequently, it would be helpful to utilize current technology to obtain a blood pressure reading for an animal. Even under current technology, if pressures are taken on a regular basis, the artifacts due to agitation of the animal and inaccuracies in the method will nevertheless enable the user to establish a baseline reading to determine if there are variations from this baseline. Even if the absolute values are not accurate, a sudden increase or decrease in the baseline measurements is important information for use by a Doctor of Veterinary Medicine, a Veterinary Technician, or an animal owner. For these reasons, a device which could measure blood pressure simply and inexpensively would be helpful.

SUMMARY OF THE INVENTION

The current invention is a thermometer probe combined with a cuff to wrap around an extremity of the animal, ordinarily the tail. The thermometer will not only have a visual display of the temperature recorded by the thermometer, but will also have a timer which can be set to sound an audible signal at a preset interval. A cuff to wrap around an extremity of an animal ordinarily the tail of an animal, will use a transducer to detect a pulse from an artery, usually the coccygeal or median caudal artery. The signals from the cuff will pass through a cord to the thermometer probe, which will display the results on a common liquid crystal display. The cuff and cord serve a dual purpose of anchoring the thermometer probe in place alleviating or eliminating the problem of a large animal which, on occasion, can suck a rectal thermometer into the rectum. A timer incorporated in the thermometer unit can sound beeps at a set interval. This allows the user of the device to count respirations without the necessity of timing the interval for which respirations are counted. Hence, if the device is set to give an audible signal at an interval, the doctor will count the respirations from the time of the first beep to a second beep, then multiply by the correct factor to get a respiration rate for the animal being examined. The invention can be equipped with circuitry which would continuously monitor the pulse rate being transmitted by the cuff to sound an audible alarm should the rate drop below a preset amount or above a preset amount. This would allow a continuous monitoring of the pulse rate by a veterinary doctor during short procedures performed on an animal which may require anesthesia.

Some models of the device may be equipped with a sphygmomanometer cuff and transducer sensor, which may be used to measure blood pressure. The device could be built in several different sizes for use with small domestic animals like cats or small dogs, up to larger models that would be used with large animals like cows or horses. The thermometric probe inserted into the rectum of the animal can be equipped with a small coil or loop for fecal sampling, which could be used to test for parasites, occult blood, and the like, obviating the need for a separate stool sampling for animals being examined. It is anticipated that in some small animals the cuff would perhaps need to be placed around a leg because some breeds of cats and dogs either have no tail or, for aesthetic reasons, the tail is cropped.

It is believed this device will find application in the offices of veterinary doctors, veterinary hospitals, animal breeders, and animal owners. The cost of an emergency visit to a veterinary office often will exceed $50.00 and may be substantially more for large animals like horses. Either a breeder of the animal or an owner could use this device to avoid unnecessary trips to a veterinary office. It will allow the lay person to monitor the condition of a chronically ill or an injured animal to better determine if intervention by a veterinary doctor is necessary. A veterinary technician in a veterinary doctor's office or in a veterinary hospital, who routinely take temperatures, pulse, and respiration will find this device highly useful. It will simplify and quicken these routine tasks and help avoid the problems involved in simultaneously counting a pulse and respiration while keeping track of an elapsed interval of time. In the devices that are equipped with a blood pressure cuff, it will make it possible to routinely determine blood pressure, an important vital sign. It can be used to monitor signs during simple veterinary procedures by veterinary doctors. The device can be built and sold at a price that will make it attractive to pet owners or animal breeders and it may be built and sold in a commercial version. It can be designed ergonomically for ease of use and made of easily cleaned materials. The commercial version will have more features, will have a heavyduty construction and will necessarily cost more, but is a clear advance in the art in veterinary medicine offices.

BRIEF DESCRIPTION OF THE DRAWINGS

FIG. 3 shows the pulse and blood pressure embodiment of the current invention.

DETAILED DESCRIPTION OF THE DRAWINGS

Figure 1A:
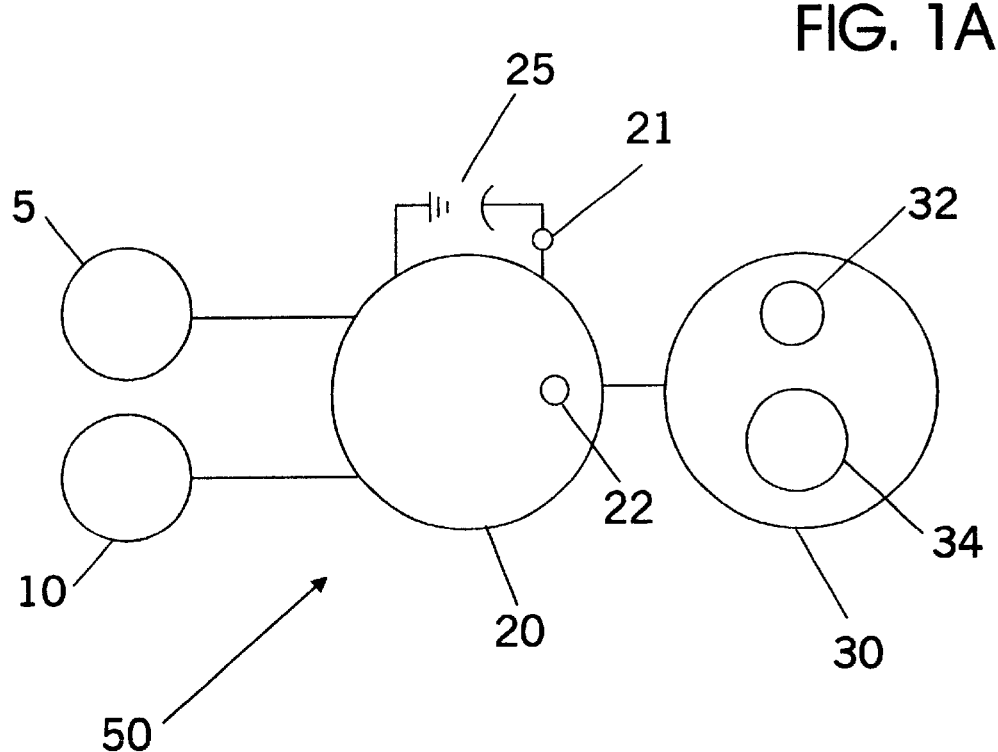
FIGS. 1A and 1B show a schematic outline of the two embodiments of the current invention.

FIG. 1A shows in schematic form the basic elements of the current vital sign monitoring system (50) in one embodiment that measures pulse, rectal temperature, and provides a timer for respirations or other timed measurements. A central processing and receiving unit (hereafter CPU) (20) is connected to a temperature sensing unit (5) and a pulse sensing unit (10). There is a power source (25) controlled by an ON/OFF switch (21) for the CPU (20) which also powers the temperature sensing unit (5) and the pulse sensing unit (10). The CPU (20) is also connected to an output unit (30). The output unit (30) has a visual display (34) and an audible alarm (32).

The temperature sensing unit (5) ordinarily will be a thermistor of the type commonly employed in digital thermometers both for animal and human use. It will be connected to the CPU (20) to transmit the sensed temperature to the CPU (20) and to receive power from the power source (25). The power source (25) powers the CPU (20) and the temperature sensing unit (5). Control of the operation of the temperature sensing unit (5) is done by the CPU (20). The CPU (20) will control the temperature sensing unit (5) and the output unit (30) and the visual display (34). For example, temperatures could be displayed in farenheight or celsius temperature scales. Control of the CPU (20) itself could be done by touch screens on the visual display (34) or by a series of pressure sensitive buttons (not shown). Typically, if pressure sensitive buttons (not shown) are used to control the CPU (20) then they would be on the underside of the vital sign monitoring system (50) so that they would not be touched or accidentally changed during ordinary operation of the unit Exactly how the CPU (20) is controlled, whether by touch screens on the visual display (34) or by buttons placed on the underside of the vital signs monitoring system (50), is a matter of choice to one of ordinary skill in the art The pulse sensing unit (10) can employ a variety of technologies to sense the pulse. In the usual practice, a nurse, veterinary technician, or doctor will find an artery, usually on the inside of the leg, of a small animal like a dog or cat, and tactually palpate the artery so that the pulse through the artery could be felt while simultaneously maintaining tactile contact with the artery. A count would be maintained of each pulse for a set interval of time. To arrive at the pulse rate per minute the counted number of pulses would be multiplied by the appropriate multiple (say four (4) for a 15-second count) to arrive at a pulse rate based on a minute of time. However, here the pulse sensor could use different means of picking up either the acoustic signal created by the pulse or the pressure variations created in the artery by the pulse beat within the artery. For example, a microphone could be used to pick up an acoustic signal. Various pressure sensors could be used to detect the change within the tension of the artery created by the pulse. The pressure sensor could be a strain gauge, an accelerometer, or various optical displacement sensors. For large animals like horses it may be possible to couple the pulse sensing unit (10) into the rectal probe which contains the thermistor used for the temperature sensing unit (5). For example, in a horse the beat of the aorta is strong enough to where it can be tactically sensed by a technician in the horse's colon. However, the pulse sensing unit (10) coupled with a thermistor in a rectal probe will not be practical for many other animals, including most small animals like dogs or cats. Consequently, it is believed that a pulse sensing unit which is placed in proximity to an artery by a cuff or similar device, ordinarily on an extremity, can be used for large animals and for small animals and is currently the most practical way of sensing a pulse. The signals from the pulse sensing unit (10) are transmitted to the CPU (20) and power for the pulse sensing unit (10) is received from the power source (25) through the CPU (20).

The CPU (20) will necessarily contain a timer or clock device, as well as calculating means. The signals from the temperature sensing unit (5) will be translated into an output for transmission to the output unit (30) by the CPU (20). The signals from the pulse sensing unit (10) will be received and recorded for an appropriate interval for transmission as a calculated pulse rate to the output unit (30). While the device is being employed to sense the pulse and the temperature, respirations will ordinarily be checked by visual observation by the technician, nurse, or doctor taking the vital signs. Consequently, a button (22) will be employed to activate a timer within the CPU (20) so that the CPU (20) will signal to the output unit (30) to sound an audible alarm by an audible alarm (32) placed in the output unit (30). This could be set by the user to sound at a particular interval. This would eliminate the need for the user of this invention to separately maintain count over the number of respirations being observed while also observing a clock to determine a particular interval. For example, respirations might be counted for a pre-determined set interval of 20 seconds. If five (5) respirations are observed for 20 seconds, then when the alarm sounds at the preset interval of 20 seconds, the user of the invention will know to stop counting respirations at that time, multiplying the result by three (3) to arrive at a respiration rate for one minute. It will only be necessary for the user to count the respirations while the preset interval is automatically counted by the CPU (20) and sounded by the audible output unit (32).

Figure 1B:
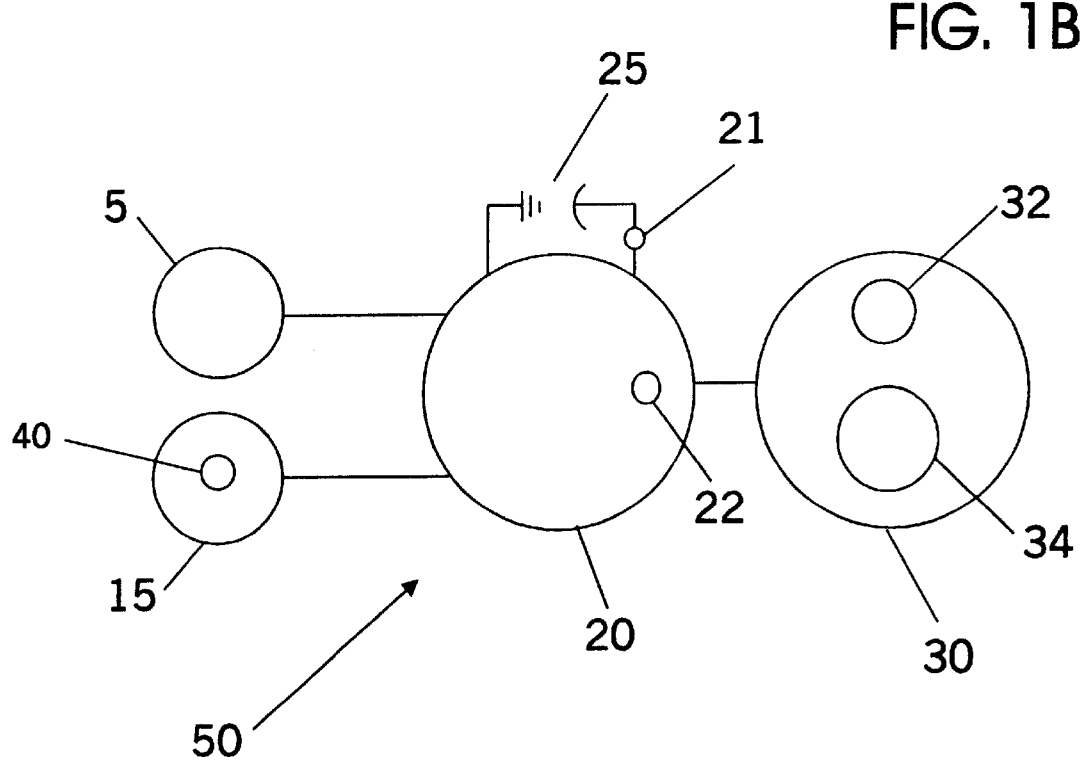

FIG. 1B shows the same device, but with an added sensing unit (15) for blood pressure. To take blood pressure in office settings in a non-invasive way, ordinarily an inflatable cuff called a sphygmomanometer is placed around an extremity—in a human the upper arm, in animals frequently a rear leg or tail, and inflated until the pressure or the cuff occludes the artery so that no pulse sound may be audibly observed. An operator monitors the pulse. A doppler signal device can be used to monitor the pulse, as can a stethoscope. When an operator can no longer detect a pulse, the pressure increase in the cuff is stopped and the pressure is gradually released from the cuff. A manometer which measures the pressure within the cuff is observed. When pulse sounds are detected once more, then the pressure within the cuff gives the systolic pressure. The cuff is continued to be deflated until the pulse becomes undetectable. The reading on the manometer is the diastolic pressure of the animal being observed.

As with measuring pulse, a variety of technologies may be employed to determine when pulse sounds become audible in response to lowering the pressure in the cuff by bleeding air from the cuff. If both the systolic and diastolic pressures are desirable, ordinarily an ultrasonic crystal that can translate pulse sound waves will be used in combination with a manometer. More than one cuff size may be required for use with different size animals. If the blood pressure sensor unit (15) is used, then the pulse rate will automatically be sensed and transmitted to the CPU (20) for display on the output unit (30) without the use of the pulse sensor (10) (seen in FIG. 1A). However, in many applications it will be neither necessary nor desirable to take the blood pressure. In that case the smaller pulse sensing unit (10) seen in FIG. 1A, which does not use a pressure cuff would be employed instead.

Within the blood pressure sensing unit (15) there is necessarily a pump which will be used to inflate and deflate the cuff necessary for the blood pressure sensing unit (15). The pump (40) ordinarily will be powered by the power source (25) which also powers the CPU (20). More specific information about the operation of the inflatable cuff, which is part of the blood pressure sensing unit (15), is seen more clearly in FIG. 3.

Figure 2:
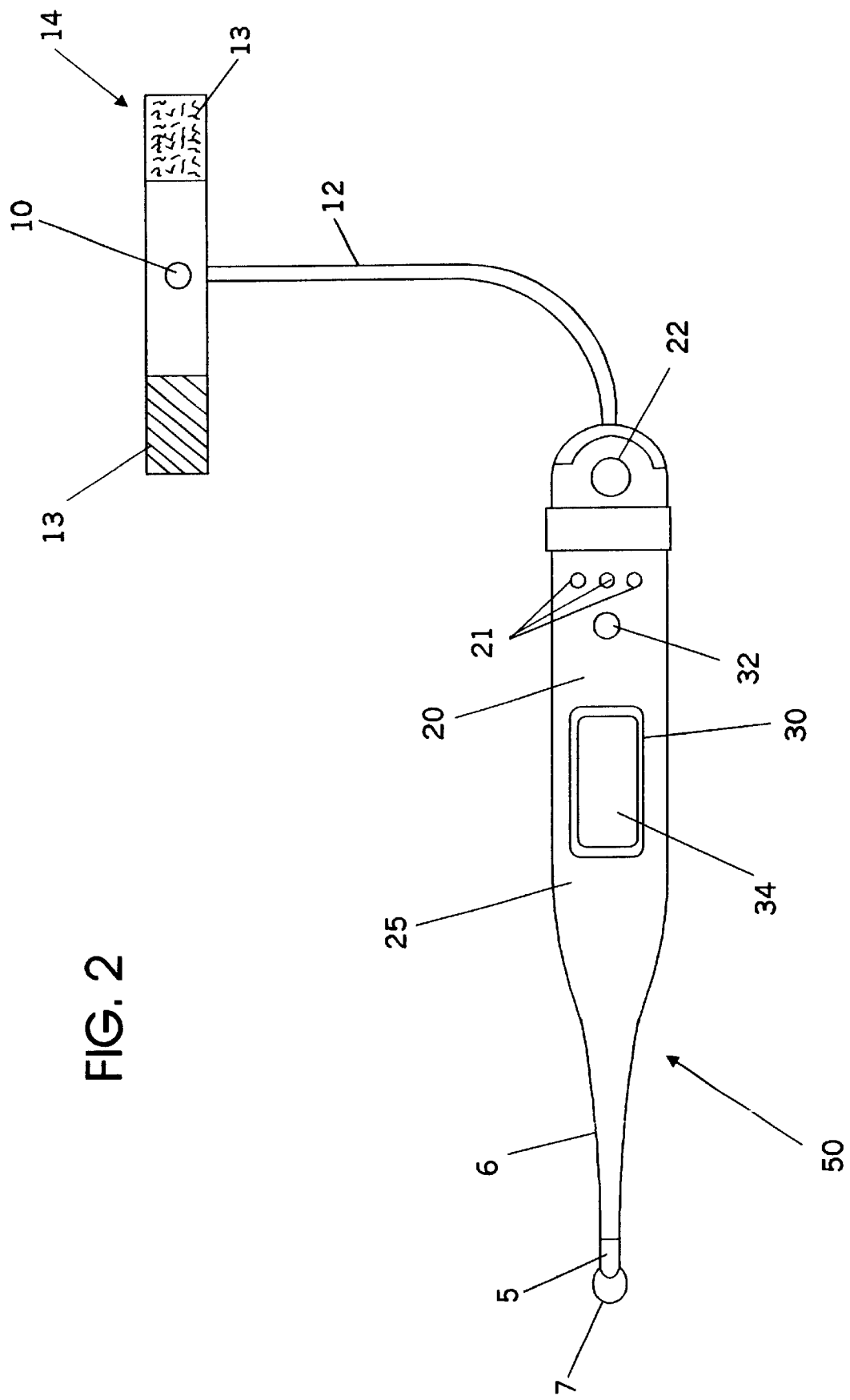
FIG. 2 shows the pulse rate embodiment of the current invention.

FIG. 2 shows a possible commercial embodiment of the vital signs monitoring system (50). Both the CPU (20) and the output unit (30) are combined in the handle of the vital signs monitoring system (50). The vital signs monitoring system (50) tapers at one end to a cylindrical rectal probe (6). At the end of the rectal probe (6) is a temperature sensing unit (5). The temperature sensing unit (5) is ordinarily a thin metal or plastic cylinder which contains a thermistor. It is necessary that the covering over the thermistor be thermically active in order to quickly transmit the temperature to the thermistor for detection and transmission to the CPU (20). A fecal loop (7) may be incorporated at the end of the temperature sensing unit (5) if one wishes to sample fecal material for diagnostic purposes. Contained within the handle of the vital signs monitoring system (50) is the CPU (20), the power source (25) (ordinarily batteries), and the output unit (30). The output unit (30) will ordinarily consist of a display screen (34). This will display the results of the temperature sensing unit (5) and the pulse sensing unit (10). There are control buttons (21) that activate the temperature sensing unit (5) and the pulse sensing unit (10) and to turn the vital signs monitoring system (50) on and off. Also contained in the handle of the vital signs monitoring system (50) is a sound output device (32). The sound output device (32) sounds an audible signal following the elapse of a predetermined time. The sound output device (32) is activated by the interval button (22).

The pulse sensing device (19) is connected to the handle of the vital signs monitoring system (50) by a cord (12). This cord (12) will ordinarily contain wires which will transmit the signal from the pulse sensing unit (10) to the CPU (20) for processing and display on the output screen (34). The cord (12) may also contain wires for transmission of power to the pulse sensing unit (10) by the power source (25) contained within the handle of the vital signs monitoring system unit (50). The pulse sensing unit (10) must be placed at or on the surface close to an artery so that either pressure variations or sound variations may be sensed by the pulse sensing unit (10). This ordinarily requires that it be placed within a support band (14) usually of a flexible woven material, which can be adjustably connected to an extremity of the animal being monitored. Usually, this is easily accomplished by connecting material (13). This can be a hook-and-eye material known by the trade name of Velcro®. The connecting material (13) will not only secure the band (14) to the extremity of the animal being monitored, but will also allow for a wide adjustment so that this same band could be used for the tail or the leg of the same animal, depending on where the user desires to place the pulse sensing unit in order to best sense the pulse in an artery of the animal being monitored.

FIG. 3 shows a second commercial embodiment of the vital signs monitoring system (50). Here, the primary difference is in the external blood pressure sensing unit (15). Here, there is an inflatable cuff (19) which is inflatable to act like a sphygmomanometer. This occludes the arteries within the extremity around which the inflatable cuff (19) is placed. Connecting material (18), usually hook-and-eye Velcro® like material, is placed at the ends of the inflatable cuff (19) so that it may be adjustably secured around the appropriate extremity. The blood pressure sensing unit (15) uses a pulse sensing unit (10) to sense when, as the inflatable cuff (19) is being deflated, the pulse sounds return. At that point, the air pressure within the inflatable cuff (19) is measured using air pump and measuring device (40). When the pulse sounds are no longer audible, the air pressure is measured again, thus obtaining both the systolic and diastolic pressures. These will be calculated and displayed on the output screen (34) by the CPU (20). Thus, both the blood pressure and pulse may be calculated and displayed by use of the same inflatable cuff (19). If it is desired only to take the pulse rate, then it will not be necessary to inflate the inflatable cuff (19), but one could simply attach it using the connecting material (18) to an appropriate extremity of the animal being monitored. The remainder of the vital signs monitoring system (50) operates the same in this embodiment as in the embodiment shown in FIG. 2. It is anticipated in a commercial embodiment of the invention that the band (14) used for the pulse sensing unit (10) and the connecting cord (12) could be interchangeable with the inflatable cuff (19) for the blood pressure sensing unit (15) and the connecting cord (17). That is, the device in some applications may be sold only with the pulse sensing unit (10) attachment or could be sold with the blood pressure sensing unit (15) as an attachment or with both attachments providing a greater flexibility of use. Moreover, it is also anticipated that in a commercial embodiment, sold primarily for veterinary offices, the unit might have both the pulse sensing unit (10) and the blood pressure sensing unit (15) attached to the device simultaneously. It is believed using current technology that an inflatable cuff (19) that occludes an artery is the most effective way of sensing blood pressure, although there are other technologies under development which can be used to sense blood pressure without occluding an artery. Also, it will be clear that different sized inflatable cuffs (19) will be required for different applications. An inflatable cuff (19) that would fit a small cat would not work for a large dog or even larger animals like cows or horses.

I claim:

1. An instrument for checking vital signs of an animal comprising:
    (a) means for sensing a temperature mounted on a probe electrically coupled to a central processing unit to record and display a temperature sensed by said means for sensing a temperature;
    (b) means for sensing a pulse electrically coupled to said central processing unit, said central processing unit to record and display a pulse sensed by said means for sensing a pulse;
    (c) a timer connected to said central processing unit whereby said central processing unit can calculate and display an elapsed time;
    (d) a means for sounding an audio signal when an elapsed time has been calculated by said central processing unit;
    (e) means for providing electrical power to said central processing unit, said means for sensing temperature, said means for sensing a pulse, and said timer;
    (f) means for controlling the operation of said central processing unit, said timing means, and said electrical power means.

2. An instrument for checking vital signs of an animal of claim 1 wherein said probe is sized and shaped to be inserted into a body cavity of an animal.

3. An instrument for checking vital signs of an animal of claim 2 wherein said probe is sized for insertion into the rectal cavity of an animal.

4. An instrument for checking vital signs of an animal of claim 1 wherein said central processing unit is housed in a handle electrically coupled to said probe and said central processing unit further comprises a means for displaying temperature, a pulse rate, and an elapsed time.

5. An instrument for checking vital signs of an animal of claim 4 wherein said instrument further comprises means for determining blood pressure, said blood pressure means electrically coupled to said central processing unit, said central processing unit further comprising a means for displaying blood pressure.

6. A compact hand-held instrument for use in home or veterinary office applications for checking the vital signs of an animal comprising:

(a) a probe mounted at a first end to a handle display unit, said probe of a definite size and shape;

(b) at a second end of the probe away from said handle display unit, a thermistor electrically connected to a central processing unit contained within said handle display unit and a timer in said handle display unit;

(c) a battery within said handle display unit, electrical connections for said thermistor, said central processing unit, and said timer to said battery whereby electrical power is supplied as required and in said central processing unit means for calculating and displaying a temperature on said handle display unit, means for calculating an elapsed time and means for sounding an audible signal when a predetermined amount of a lapsed time has occurred;

(d) an adjustable cuff with a pulse transducer in said cuff, said transducer electrically connected to said central processing unit in said handle display unit, means for calculating a pulse in said central processing unit and means for displaying said calculated pulse on said handle display whereby a user may take the temperature and pulse of an animal using said probe and adjustable cuff and use the timer to count respirations to determine a respiration rate.

7. A compact hand-held instrument for use in home or veterinary office applications for checking the vital signs of an animal of claim 6 wherein said probe is of a size and shape to be used with cats or small dogs.

8. A compact hand-held instrument for use in home or veterinary office applications for checking the vital signs of an animal of claim 6 wherein said probe is of a size and shape to be used with animals the size of a medium or large dog.

9. A compact hand-held instrument for use in home or veterinary office applications for checking the vital signs of an animal of claim 6 wherein said probe is of a size and shape to be used with horses or similar sized animals.

10. A compact hand-held instrument for use in home or veterinary office applications for checking the vital signs of an animal of claim 6 wherein said hand-held instrument further comprises means for detecting and displaying blood pressure.

11. A method for taking the vital signs of an animal comprising:

(a) placing a cuff around an extremity of an animal in proximity to an artery, in said cuff a transducer for sensing blood flow in said artery;

(b) attaching said cuff by electrical connections to a handle display unit, said handle display unit having a probe mounted at one end of said handle display unit, said probe containing a thermistor electrically connected to said handle;

(c) providing a central processing unit in said handle for calculation of a temperature and pulse and display of said temperature and said pulse on said handle display unit;

(c) placing said probe into a body cavity of an animal for a definite time whereby said thermistor may determine the body temperature of an animal;

(d) providing a timer and an alarm unit in said handle display unit so that an elapsed time of a definite duration may be calculated and an audible alarm sounded at the end of said definite time unit;

(e) counting respirations of said animal during said elapsed time and calculating a respiration rate for said animal whereby an operator may determine the pulse of an animal by use of said cuff, the temperature of an animal by use of said probe, and the respiration rate of said animal by counting the respirations as assisted by said timer all to determine the vital signs of pulse respiration rate, and temperature.

12. A method for taking the vital signs of an animal of claim 11 further comprising placing a second cuff around an extremity of an animal in proximity to an artery, in said second cuff a means for sensing the blood pressure in said artery and a means for displaying said blood pressure in said handle display unit.

* * * * *